US006248125B1

United States Patent
Helming

(10) Patent No.: US 6,248,125 B1
(45) Date of Patent: Jun. 19, 2001

(54) PERINEAL COLD BUBBLE

(75) Inventor: Tamara M. Helming, Chicago, IL (US)

(73) Assignee: Allegiance Corporation, McGaw Park, IL (US)

( * ) Notice: Subject to any disclaimer, the term of this patent is extended or adjusted under 35 U.S.C. 154(b) by 434 days.

(21) Appl. No.: 08/636,614

(22) Filed: Apr. 23, 1996

(51) Int. Cl.$^7$ ...................................................... A61F 7/00

(52) U.S. Cl. ............................................. 607/108; 607/96

(58) Field of Search ................................ 602/67; 607/96, 607/108, 112, 114, 109, 119, 111; 62/4; 126/204

(56) References Cited

U.S. PATENT DOCUMENTS

| | | |
|---|---|---|
| D. 302,592 | 8/1989 | Holmes . |
| 734,213 | 7/1903 | Barnes . |
| 1,567,931 | 12/1925 | Epler . |
| 2,323,478 | 7/1943 | Lobl . |
| 2,562,121 | 7/1951 | Poux . |
| 2,573,791 | 11/1951 | Howells . |
| 3,095,291 | 6/1963 | Robbins . |
| 3,149,943 | 9/1964 | Amador . |
| 3,175,558 | 3/1965 | Caillouette et al. . |
| 3,643,665 | 2/1972 | Caillouette . |
| 3,736,769 | 6/1973 | Petersen . |
| 3,763,622 | 10/1973 | Stanley, Jr. . |
| 3,768,480 | 10/1973 | Mesek . |
| 3,783,869 | 1/1974 | Schnipper . |
| 3,804,077 | 4/1974 | Williams . |
| 3,809,096 | 5/1974 | York . |
| 3,867,939 | 2/1975 | Moore et al. . |
| 3,871,376 | 3/1975 | Kozak . |
| 3,889,684 | 6/1975 | Lebold . |
| 3,905,367 | 9/1975 | Dapcich . |
| 3,950,158 | 4/1976 | Gossett . |
| 4,107,509 | 8/1978 | Scher et al. . |
| 4,240,436 | 12/1980 | Singleton . |
| 4,397,315 | 8/1983 | Patel . |
| 4,404,820 | 9/1983 | Romaine . |
| 4,550,725 | 11/1985 | Wishman . |
| 4,596,250 | 6/1986 | Beisang, III et al. . |
| 4,596,570 | 6/1986 | Jackson et al. . |
| 4,605,006 | 8/1986 | Jacques . |
| 4,607,624 | 8/1986 | Jefferson . |
| 4,834,739 | 5/1989 | Linker, III et al. . |
| 4,856,651 | 8/1989 | Francis, Jr. . |
| 4,911,701 | 3/1990 | Mavinkurve . |
| 4,953,550 | 9/1990 | Dunshee . |
| 5,062,425 | 11/1991 | Tucker . |
| 5,167,655 | 12/1992 | McCoy . |
| 5,178,139 | 1/1993 | Angelillo . |
| 5,184,613 | 2/1993 | Mintz . |
| 5,205,278 | 4/1993 | Wang . |
| 5,211,949 | 5/1993 | Salyer . |
| 5,245,938 | 9/1993 | Frye . |
| 5,274,865 | 1/1994 | Takehashi . |
| 5,277,180 | 1/1994 | Angelillo et al. . |
| 5,300,104 | 4/1994 | Gaudreault et al. . |
| 5,314,005 | 5/1994 | Dobry . |
| 5,342,412 | 8/1994 | Ueki . |
| 5,366,491 | 11/1994 | Ingram . |
| 5,366,492 | 11/1994 | Ueki . |
| 5,393,462 | 2/1995 | Avery . |

(List continued on next page.)

FOREIGN PATENT DOCUMENTS

| | | |
|---|---|---|
| 2 178 740 | 11/1973 | (FR) . |
| 1383536 | 2/1975 | (GB) . |
| WO 94/03132 | 2/1994 | (WO) . |

*Primary Examiner*—Michael Peffley
*Assistant Examiner*—R. Kearney
(74) *Attorney, Agent, or Firm*—Paul E. Schaafsma

(57) ABSTRACT

A device for providing therapy to the perineal and rectal areas of a patient is provided. The device can be used alone or in conjunction with an absorbent pad. The device is particularly useful for alleviating post-partum swelling and pain. Different embodiments of the device can be used to provide either hot or cold therapy to a patient.

11 Claims, 4 Drawing Sheets

U.S. PATENT DOCUMENTS

| | | |
|---|---|---|
| 5,417,276 | 5/1995 | Dobry . |
| 5,417,721 | 5/1995 | Mallasch . |
| 5,425,975 | 6/1995 | Koiso . |
| 5,441,534 | 8/1995 | MacWinnie et al. . |
| 5,447,531 | 9/1995 | Wood . |
| 5,447,532 | 9/1995 | Furuya . |
| 5,456,704 | 10/1995 | Kilcullen . |
| 5,476,490 | 12/1995 | Silver . |
| 5,476,492 | 12/1995 | Unrug . |

PERINEAL COLD BUBBLE

BACKGROUND OF THE INVENTION

1. Field of the Invention

The invention relates generally to thermal therapy devices and relates more specifically to hot and cold packs for providing thermal therapy to the perennial area of a patient.

2. Brief Description of the Prior Art

Various forms of thermal therapy have been used in the past to provide either heating or cooling to specific parts of a patient's body. For example, heat has been used in the past to increase blood flow and speed the healing process to an injured area. Similarly, cooling has been used to prevent and reduce swelling and pain. In the past, hot or cold packs have been used in a variety of applications. One application of particular interest is in providing thermal therapy to post-partum patients in the perineal and rectal areas. This therapy has been provided in a variety of ways. For example, cool therapy has been provided by placing crushed ice in a latex exam glove, closing the cuff of the glove and placing it on the perineal area. Obvious problems with using an exam glove and ice to provide cool therapy include: (1) leakage, (2) uncontrolled temperature, (3) nursing time, (4) latex allergies, (5) lack of conformity to shape of the perineal area, AND (6) uncontrolled duration of temperature. One advantage of this type of device, however, is that it is relatively inexpensive and relatively readily available.

However, due to the many disadvantages listed above, another type of device which has been developed is a combination perineal pad and cold pack in which the cold pack is located either inside or on top of the perineal pad. When the cold pack is located inside the perineal pad, the amount of cooling available to the patient is reduced due to the insulative qualities of the absorbent material. In instances in which the cold pack is fixedly attached to the top of the perineal pad, cooling is readily available, but the cold pack may not be located in the most useful location on the pad. Also, the pad may not be of the most appropriate size or absorbency for the particular patient's needs. Also, the combination of a cold pack and perineal pad can be more expensive than desired in today's cost-conscious health care environment.

Similar advantages and disadvantages exist with regard to methods and devices for providing heat therapy to the perineal and rectal areas of a patient. Two commonly used methods to provide heat therapy are: (1) moistening a towel or other absorbent device with hot water and applying it to a patient, or (2) moistening a towel or other absorbent device and then heating it in a microwave oven before applying it to a patient. Obvious disadvantages of each of these methods include potential for burning due to overheating, not achieving therapeutic heat, and presence of moisture when moisture may be contra indicated.

Therefore, a need existed to provide a device which is relatively inexpensive, easy for hospitals to use, and flexible to meet the individual needs of a particular patient. The subject invention meets all of the needs described above.

SUMMARY OF THE INVENTION

A device is provided for applying thermal therapy to the perineal or rectal area of a patient. The device includes an elongated pack to provide either heat or cold therapy. The pack has an outer shell means for placement against a patient's perineal and/or rectal area. In the preferred embodiment, the outer shell means is formed from a pliant, non-woven, fluid-impervious material. The elongated pack also includes a sealed inner space that is enclosed within the outer shell. In the preferred embodiment, the sealed space has a first compartment containing a first chemical and a second compartment containing a second chemical. In the preferred embodiment, the first and second compartments are adjacent to one another and are separated by a rupturable wall. When the wall is ruptured, the contents of the two compartments are allowed to mix to create a thermal reaction which produces a temperature in a therapeutic range. In other embodiments, the sealed inner space may be filled with a gel or other material which may be mechanically heated or cooled to a therapeutic temperature range.

DETAILED DESCRIPTION OF THE PREFERRED EMBODIMENT

Figure 1:
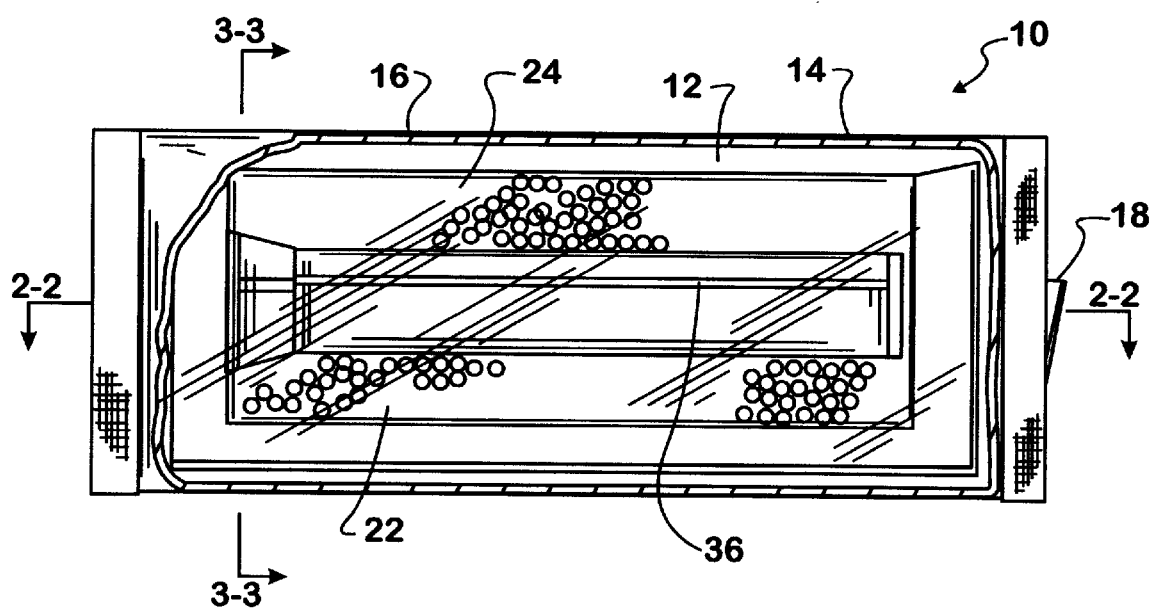
FIG. 1 is a partially broken away perspective view of the preferred embodiment of the subject invention.
Figure 2:
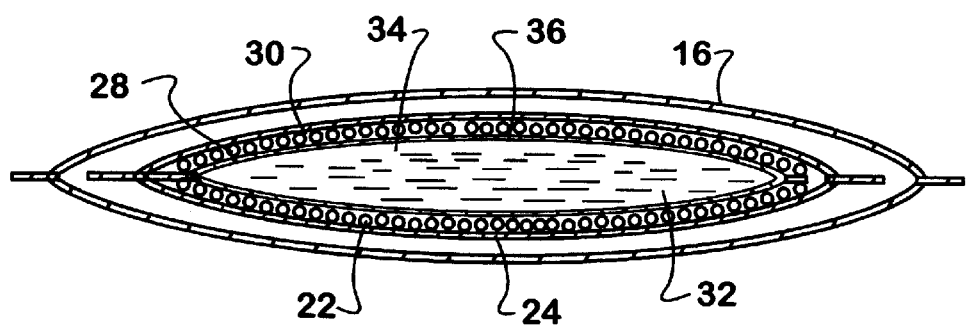
FIG. 2 is a side view of the preferred embodiment illustrated in FIG. 1 along sectional lines 2—2.
Figure 3:
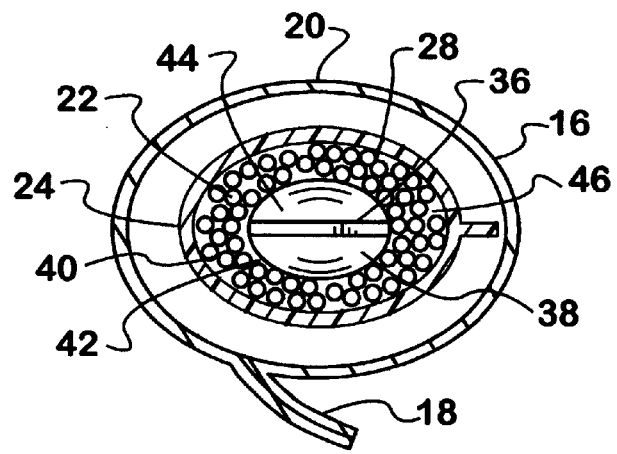
FIG. 3 is an end view of the preferred embodiment of FIG. 1.

Referring now to FIG. 1, the subject invention is a device 10 for applying herbal therapy to the perineal or rectal area of a patient. The device 10 includes n elongated pack 12 for producing a thermal treatment. In the preferred embodiment, the thermal treatment is produced through a chemical reaction of two chemical compounds which, when mixed, produce either an endothermic or exothermic reaction.

In the preferred embodiment, the pack 12 includes an outer shell means 14 for placement against a patient's perineal or rectal area. The outer shell 14 is formed of a pliant, non-woven, fluid-impervious material. Examples of such materials include co-extruded poly back non-wovens, polyester and rayon blends and spun bond. The preferred material is co-extruded poly backed non-woven. It is desirable to use a fluid-impervious material because it allows the maximum amount of thermal therapy to be available to a patient. If the outer shell 14 is a fluid-absorbent material, the fluid absorbed in the material will tend to act as an insulator against the cold or heat therapy and will reduce the effectiveness of the device 10. It is also desirable to use a pliant material to maximize the comfort of the device 10, since it is being placed against sensitive tissue. Therefore, it is highly desirable for the outer shell 14 not to include rough edges. In the preferred embodiment, the outer shell 14 is formed from a co-extruded sheet of material 16 having a single seal 18. Also, in the preferred embodiment, seal 18 is placed away from the patient's tissue so that a uniform surface 20 is in contact with the patient.

In the preferred embodiment, a sealed inner space 22 is provided within the outer shell 14. In another embodiment, the sealed inner space 22 is formed from a separate pouch 24. In yet another embodiment, the outer shell 14 can form a pouch 26 that forms both the outer shell 14 and inner space 22.

In the preferred embodiment, the sealed inner space 22 is formed of a pouch 24 made of a laminated rollstock, polyester/low-density polyethylene (LDPE). Other materials which may be used to form the pouch 24 include biaxially oriented nylon laminated to linear low density polyethylene (LLDPE) and straight polyethylene. The inner space 22 includes a first compartment 28 which contains a first chemical 30. The inner space 22 also includes a second compartment 32 containing a second chemical 34. A rupturable wall 36 is also provided between the first and second compartments 28, 32. When the rupturable wall 36 is ruptured, the first and second chemicals 30, 34 are allowed to mix to cause either an endothermic or exothermic reaction to occur. When heat therapy is desired, the first chemical 30 may be taken from the group consisting of sodium acetate and sodium thiosulfate, and the second chemical 34 may be taken from the group: consisting of borax and aluminum oxide so that when the first and second chemicals 30, 34 are exposed, an exothermic chain reaction occurs.

Similarly, when cold therapy is desired, the first chemical 30 may be taken from the group consisting of ammonium nitrate and urea, and the second chemical 34 may be taken from the group consisting of water and additives so that when the first and second chemicals 30, 34 are mixed, an endothermic reaction occurs.

In the preferred embodiment, the elongated pack 12 is generally rectangular and of a length designed to contact at least one of the perineal and rectal areas.

In another embodiment, the pack 12 may be long enough to cover both areas. In one embodiment, the first compartment 28 is formed of a rupturable sealed bubble 38. The bubble 38 is located entirely within the sealed pouch 24. The second compartment 32 is formed from an area 42 remaining between the sealed bubble 38 and the inner wall 40 of the pouch 24. Accordingly, the bubble 38 contains the first chemical 30, and area 42 contains the second chemical 34. For example, bubble 38 may contain water 44, and area 42 may contain ammonium nitrate 46. When the bubble 38 is ruptured, the ammonium nitrate 46 and water 44 mix to produce an endothermic reaction, resulting in cooling.

Figure 4:
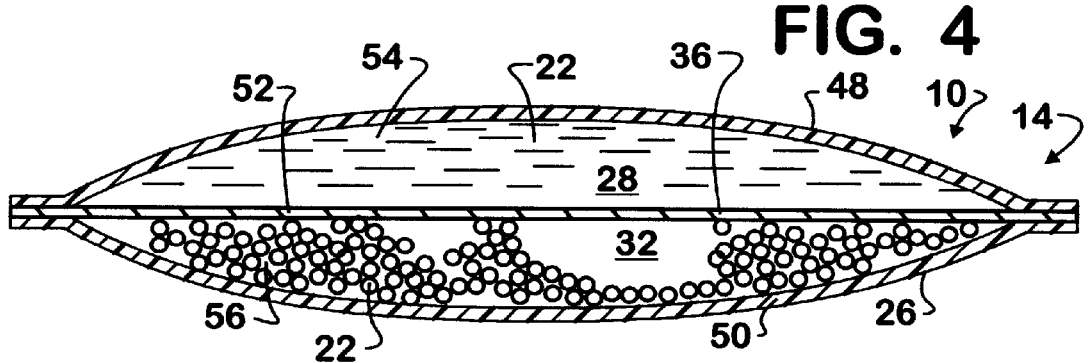
FIG. 4 is a side view of another embodiment of the invention in which a rupturable wall extends between two sheets of fluid-impervious material.

As illustrated in FIG. 4, in another embodiment of the invention, the outer hell 14 of the device 10 is formed from first and second sheets of a fluid-impervious material 48, 50. The first and second sheets 48, 50 are sealed to one another around the edges to form a sealed inner space 22. A third rupturable sheet 52 is located between the first and second sheets 48, 50. The third sheet 52 is sealed to at least one of the first and second sheets 48, 50 around the edges of the third sheet 52 so that a first compartment 28 is formed by an area 54 between the first and third sheets 48, 52 and a second compartment 32 is formed in the area 56 between the second and third sheets 50, 52.

Figure 5:
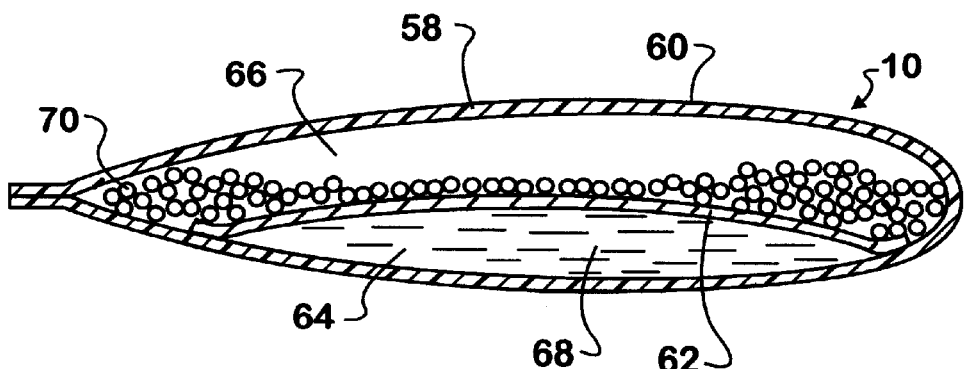
FIG. 5 is a side view of yet another embodiment of the invention in which a rupturable wall is attached to one sheet of fluid-impervious material.

Another embodiment of the invention is illustrated in FIG. 5. As can be seen in this figure, the device 10 is formed from two sheets of material. A first sheet 513 is used to form an outer shell 60. A second sheet of material 62 is a rupturable material. The second sheet 62 is sealed about its edges to the first sheet 58 to form a first compartment 64. The first sheet 58 is then folded over the second sheet 62 and sealed about its edges to form a second compartment 66. First and second chemicals 68, 70 are inserted in the first and second compartments 64, 66 respectively.

Figure 6:
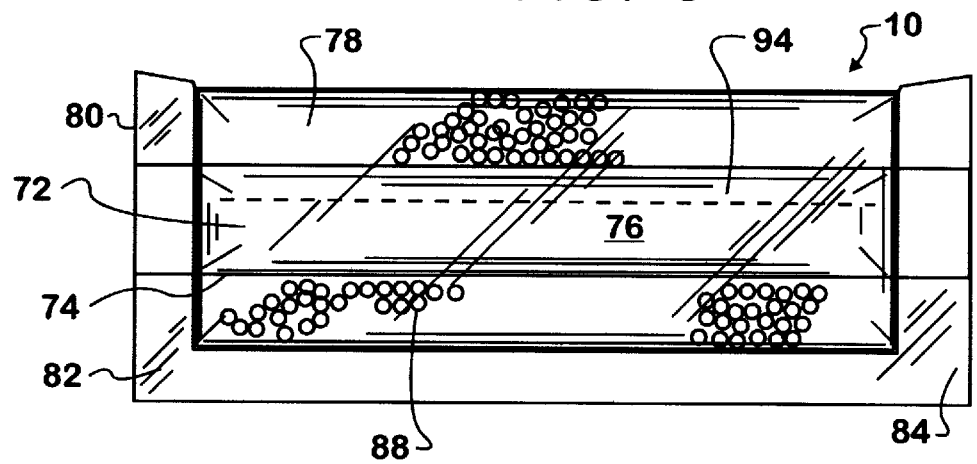
FIG. 6 is another embodiment of the subject invention in which a bubble is located inside a pouch formed of a single sheet of material and sealed about three edges.

In a particularly preferred embodiment illustrated in FIG. 6, the first compartment 72 is formed from a bubble 74 made of laminated film made of polyester/LDPE and is filled with water 76. The second compartment 78 is formed from a second single sheet 80 of polyester/LDPE. The second sheet 80 is folded to surround and encase the bubble 74. The second sheet 80 is sealed along its opposite folded edges 82, 84 to form an envelope type pouch 86 which forms the second compartment 78. The sealing encases the first compartment 72 with the second compartment 78 at the sealed edge where the first compartment 72 and the second compartment 78 overlap. The second compartment 78 is then filled with ammonium nitrate 88. The remaining edges 90, 92 between the opposite folded edges 82, 84 are then sealed to seal the second compartment 78. In the preferred embodiment, the bubble 74 has a perforated area 94 which weakens the bubble 74 and allows it to rupture prior to any rupturing of the second sheet 80. Thus, when pressure is applied to the device 10, the perforated area 94 will rupture first to allow the water 76 and ammonium nitrate 88 to mix, thereby producing the desired endothermic reaction. In other similar embodiments, other chemicals may be used as described above to produce an exothermic reaction.

Figure 7:
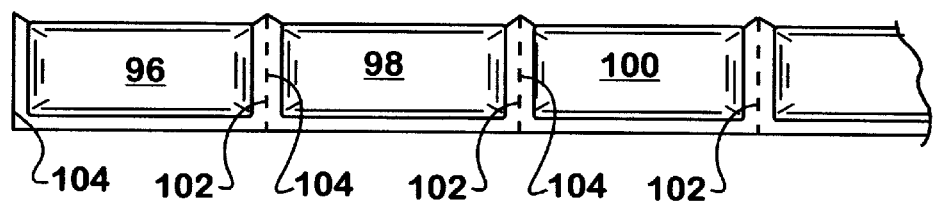
FIG. 7 is another embodiment of the invention in which multiple devices are connected to one another yet are detachable.

In another embodiment of the invention as illustrated in FIG. 7, multiple thermal packs 96, 98, 100 are connected to one another and can be detached from one another as desired. In the preferred embodiment, each pack 96, 98, 100 is generally rectangular in shape and has opposed first and second narrow ends 102, 104. A first end 102 of one pack 96 is attached to a second end 104 of an adjacent pack 98. In the preferred embodiment, a perforation 106 exists between the first and second ends 102, 104 to make the packs separable from one another.

Figure 8:
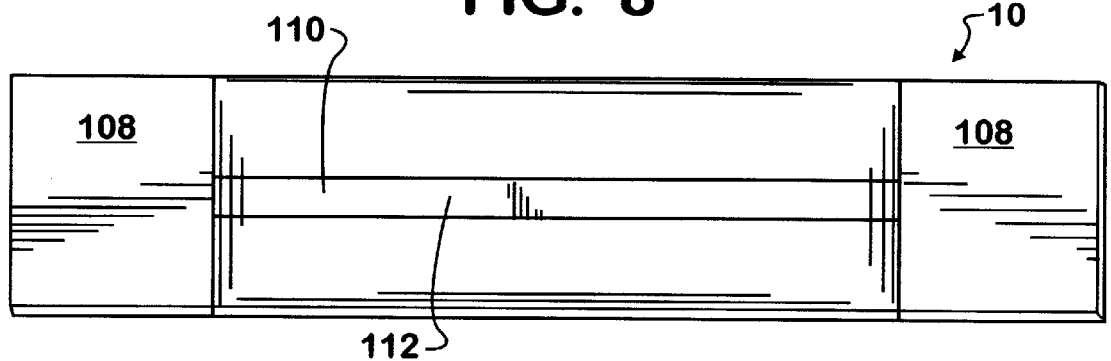
FIG. 8 illustrates another embodiment of the invention in which attachment devices are provided for placement.

In yet another embodiment illustrated in FIG. 8, each device 10 may include one or more tabs 108 which can be used to attach the device 10 to a holding mechanism such as a sanitary pad belt or other device (not illustrated). Another attachment means 110 may be provided. The attachment means 110 may be an adhesive strip 112 or other securing mechanism.

Figure 9:
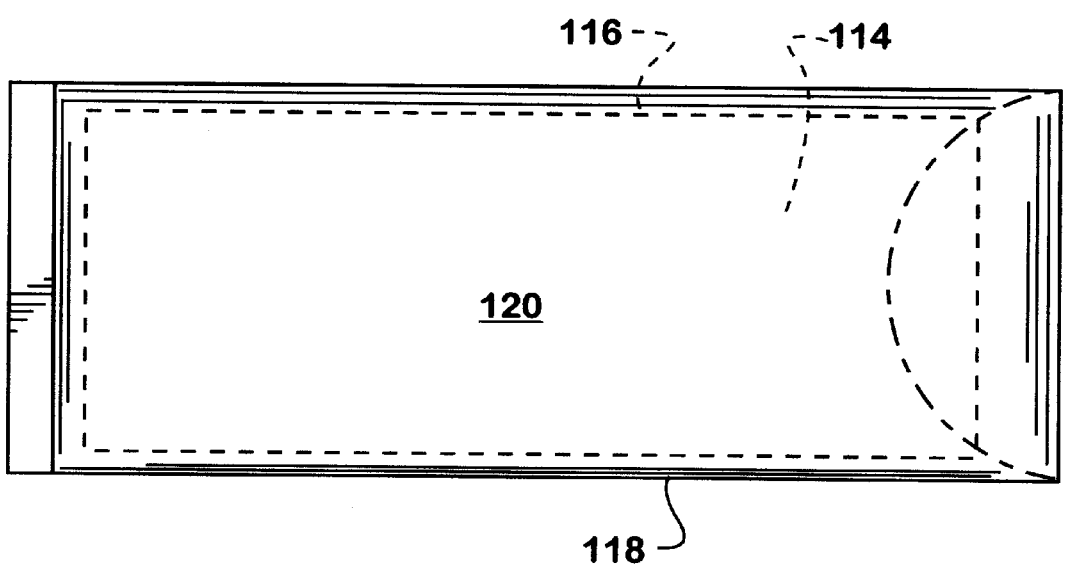
FIG. 9 illustrates another embodiment of the invention in which a reusable pouch is used with a single-use disposable outer envelope.

Finally, in another embodiment of the invention/ illustrated in FIG. 9, a reusable pouch 114 containing a gel or other material 116 can be used in conjunction with a single use disposable pouch 118. The gel 116 may be heated or cooled as desired and then placed inside of the disposable pouch 118. In this way, the possibility of cross-contamination through multiple uses of the same pouch 114 can be reduced by having a new surface 120 in contact with the patient for each use.

While the invention has been described in detail and with reference to specific embodiments thereof, it will be apparent to those skilled in the art that various changes and modifications can be made therein without departing from the spirit and scope of the invention.

I claim:

1. A device for applying thermal therapy to the perineal area of a patient, comprising:

an elongated pack to produce a thermal reaction, said pack having:

(A) an outer shell means for placement against said perineal area, said outer shell being formed of a pliant, non-woven, fluid-impervious material; and (B) a sealed inner space enclosed within said outer shell, said inner space having:
  (i) a first compartment containing a first chemical;
  (ii) a second compartment containing a second chemical;
  (iii) said first and second compartments being fixedly encased adjacent to one another;
  (iv) said first and second compartments having a rupturable wall there between which when ruptured causes said thermal reaction; and
  (v) the first compartment being fixedly encased by the second compartment at a sealed edge where the first and second compartments overlap and extending across the length of the second compartment.

2. A device as recited in claim 1 wherein:

said elongated pack is generally rectangular and of a length to contact at least one of the perineal and rectal areas.

3. A device as recited in claim 1 wherein:

said sealed inner space is formed of an outer sealed, laminated polyester/LLDPE pouch, said pouch having an outer wall surface and an inner wall surface;

said first compartment being formed of a rupturable polyester/polyethylene bubble containing said first chemical, said bubble being located inside said sealed pouch, said bubble having an outer wall; and said second compartment being formed of an area between said outer wall of said bubble and said inner wall of said pouch.

4. A device as recited in claim 1 wherein:

said outer shell means is formed from a material taken from the group consisting of co-extruded polymers and non-woven blends.

5. A device as recited in claim 1 wherein:

said outer shell means is formed from a co-extruded non-woven/polyethylene.

6. A device as recited in claim 1 wherein said outer shell means further includes:

an outer surface, said outer surface having an attachment means for attaching a portion of said shell to a surface juxtaposed to the perineal area.

7. A device as recited in claim 6 wherein said attachment means further includes:

an attachment area on said outer surface of said outer shell means for attachment to an absorbent pad.

8. A device as recited in claim 6 wherein said attachment means further includes:

an attachment area on said outer surface of said outer shell means for attachment to a garment.

9. A device as recited in claim 6 wherein said attachment means further includes:

an adhesive area.

10. A device as recited in claim 1 wherein:

said sealed inner space is formed of an outer sealed polyester/polyethylene pouch, said pouch having an outer wall surface and an inner wall surface:
  (A) said first compartment being formed of a rupturable polyester/polyethylene bubble containing said first chemical, said first chemical being water, said bubble being located inside said sealed pouch, said bubble having an outer wall; and
  (B) said second compartment being formed of an area between said outer wall of said bubble and said inner wall of said pouch, said second chemical being ammonium nitrate.

11. A device as recited in claim 1 wherein said sealed inner space is formed from:
  (A) first and second outer sheets of impervious material; and
  (B) a third rupturable sheet located between said first and second sheets, said third sheet being sealed to at least one of said first and second sheets, said outer sheets being sealed about the edges, whereby said first compartment is formed by an area between said first outer sheet and said third sheet, and said second compartment is formed by an area between said second and third sheets.

* * * * *